United States Patent [19]

Zolton et al.

[11] 4,434,093
[45] Feb. 28, 1984

[54] METHODS FOR PREPARATION OF HB$_s$AG FREE GAMMA GLOBULINS

[75] Inventors: Raymond P. Zolton, Somerville; Paul M. Kaplan, Sergeantsville; John V. Padvelskis, S. Somerville, all of N.J.

[73] Assignee: Ortho Diagnostic Systems Inc., Raritan, N.J.

[21] Appl. No.: 401,761

[22] Filed: Jul. 26, 1982

[51] Int. Cl.$^3$ ............... A61K 39/12; A61K 39/42; A61K 37/06; C07G 7/00
[52] U.S. Cl. ................................ 260/112 B; 424/89
[58] Field of Search ................ 260/112 B; 424/89

[56] References Cited

U.S. PATENT DOCUMENTS

| | | | |
|---|---|---|---|
| 2,761,811 | 9/1956 | Kupferberg | 167/84.5 |
| 3,073,747 | 1/1963 | Reid | 167/78 |
| 3,197,374 | 7/1965 | Hennessen | 167/78 |
| 3,234,199 | 2/1966 | Reid | 260/112 |
| 3,664,994 | 5/1972 | Perper | 260/112 B |
| 3,794,584 | 2/1974 | Kenin | 210/24 |
| 3,917,527 | 11/1975 | Shaltiel | 210/31 C |
| 4,136,094 | 1/1979 | Condie | 260/112 B X |
| 4,162,192 | 7/1979 | Mizuno et al. | 424/89 X |
| 4,165,370 | 8/1979 | Coval | 260/112 B X |
| 4,168,300 | 9/1979 | Andersson et al. | 260/112 B X |
| 4,181,713 | 1/1980 | McAleer et al. | 260/112 B X |
| 4,276,283 | 6/1981 | Eibl et al. | 260/112 B X |
| 4,296,027 | 10/1981 | Condie | 260/112 B |
| 4,349,539 | 9/1982 | Wampler | 260/112 B |

OTHER PUBLICATIONS

Tiollais, P. et al., Biology of Hepatitis B Virus, Science, vol. 213, 406–411, Jul. 1981.
Blumberg, B. S. et al., Australia Antigen and Hepatitis, CRC Monotopic Series, CRC Press, Cleveland, Ohio, 1982.
Gerety, R. J. et al., Tests for HBV-Associated Antigens and Antibodies, Chapter 11 of Viral Hepatitis, Ed. Vyas et al., The Franklin Institute Press, Philadelphia, PA, 1978.
Baumstark, J. S. et al., A Preparative Method for the Separation of 7S Gamma Globulin from Human Serum, Archives of Biochemistry and Biophysics 108:514–522, (1964).
Webb, A. J., A 30-Minute Preparative Method for Isolation of IgG from Human Serum, Vox Sang 23:279–290, (1972).
Stanworth, D. R., A Rapid Method of Preparing Pure Serum Gamma-Globulin.
Hoppe, H. H. et al., Prevention of Rh-Immunization, Modified Production of IgG Anti-Rh for Intravenous Application by Ion Exchange Chromatography, Vox Sang 25:308–316, (1973).
Friesen, A. D. et al., Column Ion-Exchange Preparation and Characterization of an Rh Immune Globulin for Intravenous Use, J. Applied Biochem. 3:164–175, (1981).
Johnson, A. J. et al., Removal of Hepatitis B Surface Antigen from Plasma Fractions, J. Laboratory and Clinical Medicine, 88, No. 1:91–101, Jul. 1976.
Nature, 188, 156–157, (1960), Stanworth.
Vox Sang 25:308–316, (1973), Hoppe et al.
J. of Applied Biochem. 3 (164–175), 1981, Friesen et al.
Arch. of Biochem. and Biophysics, 108, 514–522, (1964), Baumstark et al.

Primary Examiner—Howard E. Schain
Attorney, Agent, or Firm—Mark A. Hofer

[57] ABSTRACT

Methods for producing from human serum, human gamma globulin essentially free of HB$_s$Ag and products resulting therefrom. Specifically provided are ion exchange resin/buffer systems capable of effectively removing HB$_s$Ag thought to be closely correlated with viral hepatitis type B infectivity. Additional steps can include ultrafiltration to increase reduction of any virus not removed in the column passage as well as the addition of anti-HB$_g$ to substantially eliminate all infectivity.

6 Claims, No Drawings

METHODS FOR PREPARATION OF HB$_s$AG FREE GAMMA GLOBULINS

FIELD OF THE INVENTION

This invention relates to a process for the preparation of substantially HB$_s$Ag free gamma globulin.

BACKGROUND OF THE INVENTION

Numerous medical conditions require treatment via injection of gamma globulin. The manner of preparation of the gamma globulin is of critical importance, particularly in order to eliminate the chance of contracting viral hepatitis. Viral hepatitis is a debilitating disease at best and lethal at worst. Consequently, any advances made to eliminate the chance of contamination of any injectable product by this virus are of immense importance.

Hepatitis B virus is estimated to infect approximately 200 million persons worldwide. Since the base material for the production of gamma globulins often is plasma obtained from a human source, the chances of obtaining contaminated or infected plasma are significant in view of the substantial number of persons who are carriers, chronically infected and acutely infected. The infected plasma from such a person may contain not only varying amounts of viral particles but also different sizes and forms of the particles. One common form is the spherical particle which has a mean diameter of 22 nm. These spherical particles are generally devoid of DNA and represent free envelopes of the virus. Less common are the 42 nm Dane particles which represent the virion and consist of an envelope and a 27 nm nucleocapsid that contains a molecule of DNA. Free nucleocapsids may be observed in the nucleus of infected hepatocytes but are generally not found in the plasma. Infected hepatocytes have been found to synthesize excessive amounts of envelope having a half life of 3.3 days and can be found circulating throughout the body. In accordance with the different components of viral particles, different immunological markers have been identified. For example, associated with the core is an antigen commonly labelled HB$_c$Ag and an "e" antigen labelled HB$_e$Ag. The most common antigen employed for the detection of hepatitis B virus infection, however, is the surface antigen HB$_s$Ag.

HB$_s$Ag surface antigens are generally thought to be associated with the envelopes. Since immunoglobulins selective for the heptitis B surface antigen are protective against hepatitis B infection, as a consequence, the virus free envelopes present in the plasma of chronic carriers can effectively be used as a source of a vaccine. The structure and genetic organization of the hepatitis viral particle has been reviewed in an article by Tiollais et al., in Biology of Hepatitis B Virus, Science, Vol. 213, 406-411 (July, 1981). Further discussion concerning the association of the Australian antigen with persistent or chronic hepatitis may be obtained in Australia Antigen and Hepatitis by Blumberg et al., C.R.C. Monotopic Series, C.R.C. Press, Cleveland, Ohio (1982). The close relationship of hepatitis B surface antigen to hepatitis viral infectivity is discussed by Blumburg, supra, on page 14.

Historically, a number of tests have been developed for the testing and identification of hepatitis-type viral infections and are uniformly directed towards the detection of hepatitis related antigens or the antibodies specific therefor. These tests have generally been characterized as a first, second or third generation test depending upon their sensitivity in the detection of weakly positive HB$_s$Ag reference panel samples obtainable from the U.S. Bureau of Biologics. Presently, the most sensitive tests available are of the third generation category and include radioimmunoassay, enzyme linked immunosorbent asssay, reversed passive hemagglutination and reversed passive latex agglutination tests. These third generation hepatitis tests are typically capable of detecting $10^9$ HB$_s$Ag particles per ml of serum. Unfortunately, an ml of serum need contain only approximately $10^6$–$10^7$ HB$_s$Ag particles per ml in order to be infective. It thus becomes readily apparent that even a negative result with the most sensitive test available will fail to ensure the noninfectivity of a sample. Consequently, the manner of preparation for an immunoglobulin injectable reagent from a potentially infected plasma source becomes of paramount importance since any production method should ideally be capable of removing substantially all infective viral particles. At present, only in vivo chimpanzee studies are sufficiently sensitive to ensure noninfectivity of any particular sample. The cost and the requirements of such studies make them prohibitive for routine use. See "The Test for HB-Associated Antigens and Antibodies" by Gerety et al. in Chapter 11 of Viral Hepatitis, Ed. Vyas et al., The Franklin Institute Press, Philadelphia, PA (1978).

Presently, all immunoglobulin injectable materials approved for use by the FDA and Bureau of Biologics have been produced by the alcohol fractionation procedure developed by Dr. E. Cohn of Harvard during the 1940s and described in Cohn et al., J. Am. Chem. Sos., 68, 459 (1946). This procedure, coupled with the careful selection of plasma negative for hepatitis infectivity, determined by the most sensitive tests available, has been employed for such a long period of time that the U.S. government has adopted a position favoring only the resultant preparations of this procedure as safe. That the products produced by this procedure are indeed safe can easily be demonstrated by the millions of noninfected recipients of product. Unfortunately, occasional problems still arise demonstrating that despite the favorable appearance of the 'numbers' correlated with the Cohn process, the Cohn process still will not ensure complete noninfectivity. Many investigators have pointed to the development of both a plasma screening process and increasingly sensitive detection tests (to thereby eliminate source plasma having questionable infectivity) as the reason by the apparent success of the Cohn process. Despite the apparent success of the Cohn process, there is great economic pressure to develop superior production methods. The Cohn process is disadvantageous because vast volumes of plasma are required. Plasma is not only expensive but is also present only in limited supply.

It is an object of the present invention to provide a process whereby hepatitis B surface antigens may be safely eliminated from a plasma by a more efficient process than that developed by Cohn et al. The removal of HB$_s$Ag is used as a measure since it is the most highly correlated indicator of hepatitis infectivity.

Hepatitis viral particles, useful for the preparation of a vaccine, cannot be adequately grown in tissue culture and must therefore be isolated from the blood of infected persons. Purification of the hepatitis antigen from the blood is necessary in order to remove contaminating blood components which would otherwise give rise to various serum sicknesses.

Such a method for the purification of hepatitis B surface antigen is described by Mizuno et al. in U.S. Pat. No. 4,162,192. Mizuno's process involves the passage of conventionally obtained sera, hopefully containing the hepatitis B surface antigen through an anion exchange chromotography column. The column adsorbs most of the blood plasma components but allows the $HB_sAgs$ to pass freely. The effluent from this column is then subsequently passed through a cation exchanger whereby the gamma globulins are adsorbed thus leaving only the desired hepatitis B surface antigens contained in the effluent. Passage of the infected sera through the anion and cation columns provides a solution containing hepatitis B surface antigens with most blood components removed.

It is another object of the present invention, rather than provide a solution containing $HB_sAg$ free of gamma globulins, provide, instead a solution containing gamma globulins wherein all of the hepatitis B surface antigens are removed to thereby provide a safe, injectable immunoglobulin reagent.

Several conventional methods for the separation of gamma globulin from human serum have been described notably for Baumstark et al. in "A Preparative Method For The Separation of 7S Gamma Globulin From Human Serum", Archives of Biochemistry and Biophysics, 108, 514–522 (1964) and by A. J. Webb in "A 30-Minute Preparative Method For Isolation Of IgG From Human Serum", Vox Sang, 23:279–290 (1972). Although both of these papers are more concerned with the separation and selection of various gamma globulin classes from a serum containing numerous other contaminating proteins, they do address the removal of contaminating proteins and materials from the original serum sample. Both employ a DEAE-Sephadex column chromatographic material with a phosphate buffer eluting agent. Both investigators met with some degree of success as far as removal of contaminating proteins was concerned, however, both failed to address the problem of removing contaminating hepatitis viral particles in order to provide a safe, injectable reagent.

It is yet another object of the present invention to provide methods utilizing chromatographic column resin/buffer combinations which are more effective in removing contaminating hepatitis viral particles than those provided by conventional methods.

Another method, described by Stanworth in an article entitled "A Rapid Method Of Preparing Pure Serum Gamma Globulin", Nature, 188, 156–157 (1960), involves the use of a diethyl amino ethyl cellulose anion exchanger to remove proteins from human serum dialyzed to remove high molecular weight proteins, however, the method described fails to account for the effect on hepatitis viral contaminants and additionally fails to provide an injectable reagent, both of which are objects of the present invention.

Condie has described in U.S. Pat. No. 4,136,094, "Preparation of Intravenous Human and Animal Gamma Globulins And Isolation Of Albumin", another method for obtaining gamma globulin which is claimed safe for intravenous administration. Condie's method involves three manipulations including plasma stabilization by treatment with fumed colloidal silica, isolation and elution of gamma globuin and albumin from ion exchange resins and finally concentration dialysis and sterile filtration. The fumed colloidal silica step is provided to remove hepatitis associated antigen present in the plasma as well as a number of proteolytic enzymes and their precursors. The colloidal silica treated materials were tested for presence of hepatitis associated antigen by radioimmunoassay. The materials tested negative and intravenous administration of large quantities (in excess of 30 g) in over 50 patients showed no evidence of passage of hepatitis virus nor produced cases of hepatitis. To be noted, however, as previously discussed, testing by presently available radioimmunoassay procedures will not ensure that the tested sample is free of infective hepatitis. Without further testing, any such material will not be approved by the U.S. government for widespread use in excess of that required for limited clinical studies.

It is still another object of the present invention to provide a significantly simpler, effective procedure for isolating immunoglobulins from blood serum and hepatitis associated antigens which does not require fumed colloidal silica.

Treatment of hemolytic disease of the fetus or newborn has become rather standard and is accomplished by treatment of the mother by injection of Rho (D) immunoglobulin of human origin. Such a product is RhoGAM, available from the assignee hereof, operates by preventing the unimmunized Rho (D) negative mother from responding to Rho (D) antigen present on red cells and 'received' at delivery from an Rho (D) positive infant. Thus, by preventing anti-Rho (anti-D) production by the mother at delivery, the subsequent Rho (D) positive infant of this mother is protected from hemolytic disease of the newborn. Although this successful product is presently produced by a Cohn alcohol fractionation type process, several investigators have attempted to use alternative methods to produce similar materials to thereby provide an economically more advantageous product, to reduce large plasma requirements and to obtain superior protection against the threat of hepatitis infection. Such investigational efforts have been reported by Hoppe et al. in "Prevention of Rh Immunization Modified Production of IgG Anti-Rh For Intravenous Application By Ion Exchange Chromatography", Vox Sang, 25:308–316 (1973) and Friesen et al. in "Column Ion-Exchange Preparation and Characterization of an Rh Immune Globulin for Intravenous Use", Journal of Applied Biochemistry, 3, 164–175 (1981).

Hoppe in Germany and Friesen in Canada both employed a DEAE-Sephadex chromatography column in conjunction with a phosphate buffer eluding agent. Hoppe's source of anti-D containing plasma was from volunteers who passed an $HB_sAg$ laboratory test for at least six months, the plasma being stored in the interim. Thus, Hoppe employed a relatively safe, noninfective plasma to start with. No additional tests were run, however, to determine the efficacy of the DEAE-Sephadex resin/phosphate buffer combination for the removal of hepatitis B surface antigen. Hoppe's concern was instead directed towards the removal of aggregated materials and the isolation of an unfragmented, immunoelectrophoretically pure IgG having a relatively high antibody concentration. The Freisen publication reports on the modifications made to the Hoppe method for the development of an intravenous Rh IgG for use in Canada. As Hoppe had done, Freisen tested each unit of Rh plasma for $HB_sAG$ to eliminate any donors testing positive. Freisen employed the radioimmunoassay kit from Abbott Laboratories, North Chicago, Ill. (Ausria II Kit). This test is still regarded as one of the most sensitive and was also employed in the development of the invention described later. Freisen reported that clinical trials showed the material produced using the DEAE-Sephadex resin/phosphate buffer combination was effective and safe for the prevention of Rh immunization. Freisen, however, reported no additional tests for determining the efficacy of the DEAE-Sephadex/phosphate buffer combination for removing hepatitis B surface antigen from plasma samples. This, at least from the U.S. government's perspective, is especially important since the radioimmunoassay test employed in screening the donor plasma samples is incapable of detecting concentrations of $HB_sAG$ particles two or three orders of magnitude lower which may still be infective. It is this concern for the potential infectivity of a reagent produced by such a method that the United States government has been significantly more restrictive in permitting the production of injectable immunoglobulin reagents by solid phase methodologies.

It is an object of the present invention to provide resin/buffer systems that are superior in their ability to eliminate hepatitis B surface antigen than those employed by Hoppe or Friesen.

SUMMARY OF THE INVENTION

In accordance with the principles and objectives of the present invention, there are provided methods for the removal of substantially all hepatitis B surface antigens from a gamma globulin containing body fluid. Such a removal is effectuated by the application of the body fluid to a column having packed therein either DEAE-Sephadex or QAE-Sephadex resin and then eluting with 0.02 M phosphate buffer or approximately 0.05 M Imidazole buffer if the resin selected is QAE-Sephadex or approximately 0.04 M Tris buffer which may be used with either resin. The buffers are preferably adjusted to a pH of approximately 7.5. Effluent from the columns is monitored for the presence of protein, typically by optical measurement at 280 nm, and those fractions containing protein are collected and pooled. The protein fractions will contain substantially $HB_sAg$ free gamma globulin.

It has been additionally found advantageous to employ a proportional amount of resin at least equal to 80 mg per ml of a 1:2 diluted body fluid.

The resin/buffer combinations of the present invention have typically been found significantly more effective than the DEAE-Sephadex-phosphate buffer combination used by traditional methods to remove hepatitis B surface antigen as supported by the test data presented hereafter.

DETAILED DESCRIPTION OF THE INVENTION AND BEST MODE

Because of the United States government's justifiable concern regarding the safety of immunoglobulin preparations produced for injection into persons, the selection of solid phase purifying materials and eluting reagents is critical if eventual government-approved, commercial production is to be realized. Consequently, substantial in vitro tests have been completed and are described hereafter. Because of the limited sensitivity of the best $HB_sAg$ detection tests available to date, a guiding principle used was that any process employed to remove hepatitis B surface antigen must be shown to remove at least 2–3 orders of magnitude (i.e., 100–1000 $HB_sAg$ particles/ml) to thereby bridge the gap between the sensitivity of the hepatitis B surface antigen test and the threshold of infectivity.

Four chromatographic columns ($0.9\times15$ cm columns of acrylic plastic available from Pharmacia Fine Chemicals) were separately prepared to contain one of the four tested resin buffer systems (QAE-Sephadex/Tris, DEAE-Sephadex/Tris, DEAE-Sephadex/phosphate or QAE-Sephadex/phosphate). The buffers employed were 0.02 M phosphate and 0.04 M Tris buffers, both at a pH of 7.5 and a conductivity of $2\times10^{-3}$ mhos at 5° C. The buffers were of reagent grade quality and obtained from Mallinckrodt and Sigma respectively. The buffers were pumped through the column with a Varioperpex II Unit from L.K.B. Instruments, Inc. and the effluent monitored at 280 nm with a Unicord II Model 8300 also from L.K.B. Instruments, Inc. Results were recorded on an L.K.B. Instruments, Inc. Model 6520-7six channel D.C. recorder. The ion exchange resins, DEAE-Sephadex (Lot 13716) and QAE-Sephadex (Lot 1509) obtained from Pharmacia Fine Chemicals, were washed and equilibrated with either phosphate or Tris buffer according to the combination to be employed. The final resin concentration was 20 mg/ml. Each column, containing approximately 8 ml or 240–320 mg of packed resin after loading, was washed with two volumes of the appropriate buffer at a flow rate of 30 ml per hour.

Hepatitis positive plasma ("hot" plasma) was obtained from a chronic hepatitis B infected patient whose virus surface antigen concentration was approximately 200 mg/ml. The patient was Type A, Rh negative and the hepatitis was subtype Ay. Hepatitis B surface antigen detection was determined with a radioimmunoassay kit (Ausria II-125) commercially available from Abbott Laboratories. As recommended by Abbott Laboratories, procedure B was employed.

The plasma was prepared for application to the column by first centrifuging at 4° C. and 4,229 g (5,000 rpm on a Sorvall centrifuge) to remove cold insolubles. The sample was then diluted 1:1 and the pH adjusted to 7.5. Three mls of this diluted material was applied to the column and after entering the resin, the appropriate column buffer was pumped through. The effluent was monitored for OD 280 nm absorption and all effluent portions having a shifted baseline were collected. Typically, the volume of this peak was 16 ml$\pm$1 ml. Additional 20 ml of column buffer was permitted to pass over the resin thereby ensuring removal of unbound protein. This process of loading 3 ml of cold insoluble supernatent to the column and eluting was repeated until 5 separate peaks were collected for each of the four resin buffer systems.

The collected peaks were diluted with a buffer containing 5% bovine serum albumin in 0.01 M imidazole—0.16 M sodium chloride at a pH 7.5 for third generation RIA testing for $Hb_sAg$ content. The results were plotted as log of dilution against log of counts to allow equivalent dilutions of column peaks to be determined from linear regression of the precolumn sample.

The results obtained from the resin buffer combination systems are represented in the accompanying Table I. The "System" column indicates the resin/buffer combination (QAE is understood to mean QAE-Sephadex and DEAE is understood to means DEAE-Sephadex). The first application of sample to the virgin resin/buffer system is indicated by the (I) following the combination. The second loading of sample onto the column following a wash period is indicated by (II) and similarly the third application or loading of sample is indicated by (III).

Gerety et al., supra, have reported that the minimal safety factor of any system should be about $10^3$ reduc-

TABLE I

| System | Equivalent Dilution of "hot" plasma (1) Applied to col. | $HB_sAg$ conc. in col. effluent fraction (2) (ng/ml) | Peak Fraction vol. (ml) | Total $HB_sAG$ in peak fraction (3) (ng) | % $HB_sAg$ Removed (4) | Reduction in $HB_sAG$ conc. (5) |
|---|---|---|---|---|---|---|
| QAE-Tris (I)    | $1.18 \times 10^6$ (1a)   | 0.17   | 16.4 | 2.8         | 99.9991 (6) | $1.07 \times 10^5$ |
| QAE-Tris (II)   | $3.08 \times 10^5$ (1a)   | 0.65   | 16.4 | 13.4        | 99.9978     | $4.48 \times 10^4$ |
| QAE-Tris (III)  | $1.05 \times 10^2$ (1b)   | 1905.0 | 16.4 | 31,251.5    | 96.5276     | $2.88 \times 10^1$ |
| QAE-Phos (I)    | $1.05 \times 10^6$ (1a)   | 0.19   | 14.0 | 2.7         | 99.9991 (6) | $1.11 \times 10^5$ |
| QAE-Phos (II)   | $2.30 \times 10^5$ (1a)   | 0.87   | 15.2 | 15.9        | 99.9974     | $3.77 \times 10^4$ |
| QAE-Phos (III)  | $2.44 \times 10^2$ (1b)   | 819.7  | 14.0 | 11,491.3    | 98.7232     | $7.83 \times 10^1$ |
| DEAE-Tris (I)   | $8.87 \times 10^5$ (1a)   | 0.23   | 16.4 | 3.7         | 99.9988     | $8.11 \times 10^4$ |
| DEAE-Tris (II)  | $2.29 \times 10^2$ (1b)   | 873.40 | 16.4 | 14,326.8 (7)| 97.6122     | $4.19 \times 10^1$ |
| DEAE-Phos (I)   | $4.48 \times 10^3$ (1b)   | 44.60  | 10.2 | 455.4       | 99.8482     | $6.59 \times 10^2$ |
| DEAE-Phos (II)  | $1.0 \times 10^2$ (1b,8)  | >2000  | 13.4 | 27,255.4    | 95.46       | $2.20 \times 10^1$ |

(1) Dilution obtained from standard curve of known dilutions of "hot" sample.
(1a) Average of two trials.
(1b) Single trial values.
(2) Determined by dividing the starting $HB_sAg$ conc. of 200,000 ng/ml by the equivalent dilution factor for each system.
(3) Determined by multipyling $HB_sAg$ conc. in peak fraction by its volume.
(4) Determined by following formula:

$$\% \text{ reduced} = \frac{HB_sAg \text{ conc. in applied fraction} - HB_sAg \text{ in peak fraction} \times 100}{HB_sAg \text{ conc. in applied fraction}}$$

(5) Determined by dividing amount of $HB_sAg$ in applied fraction by total amount of $HB_sAg$ in peak fraction.
(6) These fractions were negative for $HB_sAg$ when tested by confirmation test in Abbott's kit.
(7) Value shown is cumulative.
(8) Approximate value extrapolated due to off scale readings. Other values rely on this approximation and are therefor less accurate than those figures for other systems and sample applications.

On a purely percentage basis, it would appear that all four resin/buffer systems, at least with regards to the first loading of a virgin column, are similarly effective in removing hepatitis B surface antigen. These percentages, however, mask the true facts and examination of 'real numbers' will show that, particularly because of the very large starting concentration of hepatitis B surface antigens of 200,000 ng/ml, true discrimination between resin/buffer systems can be accomplished. For instance, by examining the column entitled "Total $HB_sAg$ in peak fraction in nanograms", it is apparent that from an application of 300,000 ng of sample (1.5 ml of 200,000 ng/ml), only 2.8 ng, 2.7 ng, and 3.7 ng, were measurable in the peak fractions obtained from the column in the QAE-Tris, QAE-Phosphate and DEAE-Tris resin/buffer system combinations respectively. In contrast, the first loading of the DEAE-Phosphate resin/buffer system (employed in conventional techniques) shows its relative undesirability as indicated by the large fraction, 455.4 ng in the peak, of $HB_sAg$ passing through the column.

Comparing within systems and against different resin/buffer systems, the results in the second and third loadings shows the relative resistance of the top three resin/buffer systems to saturation levels of sample hepatitis B surface antigen loading. Clearly, the QAE-Sephadex resin appears to have a higher affinity for surface antigen making the selection of the buffer less critical than with the relatively lower efficient DEAE-Sephadex resin. Also clear is that the combination of DEAE-Sephadex/Phosphate buffer is the least effective system in removing hepatitis B surface antigen since the concentration of HBsAG in the peak fraction after column treatment is at least 200 times greater than that in any of the other systems. After a second loading, the DEAE/Phosphate combination clearly shows its inability to withstand a large onslaught of contaminating HBsAg component. Reduction in $HB_sAg$ concentration (last column of Table I) is thus more reflective of the columns capability of removing $HB_sAg$ than percentages alone.

tion of surface antigen concentration in order to bridge the test sensitivity-infectivity gap. From Table I, it is apparent that the QAE-Phosphate, QAE-Tris and DEAE-Tris resin/buffer systems for first applications, are all reducing surface antigen concentration by approximately $10^5$ thereby providing a safety factor of approximately $10^2$ reduction. Only the QAE-Tris and QAE-Phosphate systems provided an adequate safety factor in the event of a second column loading by removing more than 99.98% of the hepatitis surface antigens. The other systems failed to offer necessary protection in those circumstances. It was further discovered that the ratio of resin per ml of applied sample should ideally be no lower than 160 mg/ml to ensure adequate removal of surface antigen. However, because of the ionic strength of an undiluted sample, it was found preferable to dilute the sample one to two with water in order to avoid shrinkage. In this event, the ratio proportion would be no lower than 80 mg of packed resin per ml of one to two diluted sample. Other methods for reducing ionic strength of the sample may be employed such as dialysis, however, in an effort to reduce handling of intentionally highly infectious samples, a simple dilution was effected for the trials of the present invention.

A post filtration step of the collected column effluent through a membrane having a nominal molecular weight cutoff of $1 \times 10^6$ daltons should further increase reduction of any virus which may appear in the column effluent. Tabor et al. have reported the removal of hepatitis B virus by the presence of anti-$HB_g$ in heat-labile clotting factor concentrates. See The Lancet, July 12, 1980, page 68. Thus, by additionally providing anti-$HB_g$ to the resin/buffer treated materials, a gamma globulin product satisfying the FDA and Bureau of Biologics Safety requirements should be obtained.

Although the foregoing examples and trials illustrate the preferred mode of the instant invention, it is to be understood that the principles and scope of the invention are not to be so limited.

What is claimed is:

1. A method for removing substantially all $HB_sAg$ from a gamma globulin containing body fluid comprising the steps of:
   (a) providing the gamma globulin containing body fluid desired to be purified;
   (b) applying the body fluid to column means containing an effective amount of resin selected from the group consisting of DEAE-Sephadex and QAE-Sephadex;
   (c) eluting the body fluid from the column with a buffer selected from the group consisting of approximately 0.02 M phosphate buffer if the resin selected is QAE-Sephadex and approximately 0.04 M Tris buffer if the resin selected is DEAE-Sephadex or QAE-Sephadex, each buffer adjusted to a pH of approximately 7.5;
   (d) monitoring the column effluent for the presence of protein;
   (e) collecting, responsive to monitoring, the protein containing effluent whereby substantially $HB_sAg$ free gamma globulin is obtained.

2. The method as provided in claim 1 wherein the effective amount of resin is an amount at least equal to 160 mg/ml of body fluid.

3. The method as provided in claim 2 wherein the resin is QAE-Sephadex and the buffer is 0.02 M phosphate buffer.

4. The method as provided in claim 2 wherein the resin is QAE-Sephadex and the buffer is approximately 0.04 M Tris buffer.

5. The method as provided in claim 2 wherein the resin is DEAE-Sephadex and the buffer is approximately 0.04 M Tris buffer.

6. A method for removing substantially all $HB_sAg$ from a gamma globulin containing body fluid comprising the steps of:
   (a) providing the gamma globulin contained body fluid desired to be purified;
   (b) applying the body fluid to a column means containing QAE-Sephadex in an amount at least equal to 160 mg/ml of body fluid;
   (c) eluting the body fluid from the column with approximately 0.05 M Imidazole buffer adjusted to a pH of approximately 7.5;
   (d) monitoring the column effluent for the presence of protein;
   (e) collecting, responsive to monitoring, the protein containing effluent whereby substantially $HB_sAg$ free gamma globulin is obtained.

* * * * *